US005506343A

United States Patent [19]
Kufe

[11] Patent Number: 5,506,343
[45] Date of Patent: Apr. 9, 1996

[54] ANTIBODIES SPECIFIC FOR THE DF3 CARCINOMA ASSOCIATED ANTIGEN

[75] Inventor: Donald Kufe, Wellesley, Mass.

[73] Assignee: Dana-Farber Cancer Institute, Inc., Boston, Mass.

[21] Appl. No.: 328,536

[22] Filed: Oct. 25, 1994

Related U.S. Application Data

[63] Continuation of Ser. No. 868,352, Apr. 13, 1992, abandoned.

[51] Int. Cl.$^6$ .......................... C07K 16/30; C07K 16/46; A61K 39/395; A61K 39/44

[52] U.S. Cl. .................................... 530/387.7; 530/388.8; 530/388.85; 530/387.9; 530/391.1; 530/391.3; 435/7.1; 435/7.23

[58] Field of Search .............................. 424/130.1, 134.1, 424/138.1, 139.1, 141.1, 152.1, 155.1, 156.1, 178.1, 181.1, 183.1; 435/7.1, 7.23; 530/387.1, 387.7, 387.9, 388.1, 388.8, 388.85, 391.1, 391.3, 391.5, 391.7, 391.9

[56] References Cited

U.S. PATENT DOCUMENTS

| | | | |
|---|---|---|---|
| 4,675,382 | 6/1987 | Murphy | 530/350 |
| 4,894,227 | 1/1990 | Stevens et al. | 424/85.2 |
| 4,963,484 | 10/1990 | Kufe | 435/69.3 |
| 5,053,489 | 10/1991 | Kufe | 530/350 |

OTHER PUBLICATIONS

Waldmann Science 252:1657–1662 (1991).
Hopp: J. Immunol. Methods 88:1–18 (1986).
Harlow & Lane: Antibodies, A Lab Manual, Cold Spring Harbor, 1988.
Houghton et al. Seminars in Oncology 13:165–179 (1986).
Gendler et al. J. Biol Chem. 263:12820–12823 (1988).
Abe et al. Biochem. & Biophys. Res. Commun. 165:644–649 (1989).
Apostolopoulos et al., Production of Anti–breast Cancer Monoclonal Antibodies Using a Glutathione–S–Transferase–MUC1 Bacterial Fusion Protein, British J. Cancer 67:713–720, 1993.
Fontenot et al., Biophysical Characterization of One–, Two–, and Three–Tandem Repeats of Human Mucin (muc–1) Protein Core, Cancer Research 53:5386–5394, 1993.
Kotera et al., Humoral Immunity Against a Tandem Repeat Epitope of Human Mucin MUC–1 in Ser from Breast, Pancreatic, and Colon Cancer Patients, Cancer Research 54:2856–2860, 1994.
Price et al., Immunological and Structural Features of the Protein Core of Human Polymorphic Epithelial Mucin, Molecular Immunology 27:795–802, 1990.
Xing et al., Monoclonal Antibodies Reactive with Mucin Expressed in Breast Cancer, Immunol. Cell Biol. 67:183–195 1989.
Xing et al., Effect of Variations in Peptide Sequence on Anti–Human Milk Fat Globule Membrane Antibody Reactions, Immunology 72:304–311, 1991.
Xing et al., Second Generation Anti–MUC1 Peptide Monoclonal Antibodies, Cancer Research 52:2310–2317, 1992.
Xing et al., Epitope Mapping of Anti–Breast and Anti–Ovarian Mucin Monoclonal Antibodies, Molecular Immunology 29:641–650, 1992.
Abe, et al., Identification Of A Family Of High Molecular Weight Tumor–Associated Glycoproteins, J. Immunol. 139:257–261, 1987.
Abe, et al., Structural Analysis Of The DF3 Human Breast Carcinoma–Associated Protein, Cancer Res., 49:2834–2839, 1989.
Arklie, et al., Differentiation Antigens Expressed By Epithelial Cells in the Lactating Breast Are Also Detectable In Breast Cancers, Int. J. Cancer 28:23–29, 1981.
Bird, et al., Single–Chain Antigen–Binding Proteins, Science, 242:423–426, 1988.
Burchell, et al., A Short Sequence, Within The Amino Acid Tandem Repeat Of A Cancer–Associated Mucin, Contains Immunodominant Epitopes, Int. J. Cancer 44:691–696, 1989.
Burchell, et al., Development And Characterization Of Breast Cancer Reactive Monoclonal Antibodies Directed To The Core Protein Of The Human Milk Mucin, Cancer Res. 47:5476–5482, 1987.
Cawley, et al., Epidermal Growth Factor–Toxin A Chain Conjugates: EGF–Ricin A Is A Potent Toxin While EGF–Diphtheria Fragment A Is Nontoxic, Cell 22:563–570, 1980 (Part 2).
Chang, et al., Artificial Hybrid Protein Containing A Toxic Protein Fragment And A Cell Membrane Receptor–Binding Moiety In A Disulfide Conjugate, J. Biol. Chem. 252:1515–1522, 1977.
Chaudhary, et al., Activity Of A Recombinant Fusion Protein Between Transforming Growth Factor Type $\alpha$ and Pseudomonas Toxin, Proc. Natl. Acad. Sci. USA 84:4538–4542, 1987.
Croghan, et al., Tissue Distribution Of An Epithelial And Tumor–Associated Antigen Recognized By Monoclonal Antibody F36/22, Cancer Res. 43:4980–4988, 1983.
Hayes, et al., Genetically Determined Polymorphism Of The Circulating Human Breast Cancer–Associated DF3 Antigen, Blood 71:436–440, 1988.
Hayes, et al., Comparison Of Circulating CA15–3 And Carcinoembryonic Antigen Levels In Patients With Breast Cancer, J. Clin. Oncol. 4:1542–1550, 1986.
Hilkens, et al., Biosynthesis of MAM–6, An Epithelial Sialomucin, J. Biol. Chem. 263:4215–4222, 1988.
Hilkens, et al., Monoclonal Antibodies Against Human Milk–Fat Globule Membranes Detecting Differentiation Antigens Of The Mammary Gland And Its Tumors, Int. J. Cancer 34:197–206, 1984.

(List continued on next page.)

Primary Examiner—Margaret Parr
Assistant Examiner—Phillip Gambel
Attorney, Agent, or Firm—Fish & Richardson

[57] ABSTRACT

A monoclonal antibody which binds preferentially to unglycosylated DF3 antigen, compared to mature DF3 antigen, and which is specific for an epitope within the following amino acid sequence: $T_7R_8P_9A_{10}P_{11}G_{12}S_{13}$, which epitope includes a proline at position 11.

24 Claims, 4 Drawing Sheets

OTHER PUBLICATIONS

Hilkens, et al., Complexity of MAM-6, An Epithelial Sialomucin Associated With Carcinomas, Cancer Res. 49:786–793, 1989.

Hull, et al., Oligosaccharide Differences In The DF3 Sialomucin Antigen From Normal Human Milk And The BT-20 Human Breast Carcinomas Cell Line, Cancer Commun. 1:261–267, 1989.

Karlsson, et al., A Genetic Polymorphism Of A Human Urinary Mucin, Ann. Hum. Genet. 47:263, 1983.

Kufe, et al., Differential Reactivity Of A Novel Monoclonal Antibody (DF3) With Human Malignant Versus Versus Benign Breast Tumors, Hybridoma, 3:223–232, 1984.

Lundy, et al., Monoclonal Antibody DF3 Correlates With Tumor Differentiation And Hormone Receptor Status In Breast Cancer Patients, Br. Cancer Res. Treat. 5:269–276, 1985.

Sekine, et al., Purification And Characterization Of A High Molecular Weight Glycoprotein Detectable In Human Milk And Breast Carcinomas, J. Immunol. 135:3610–3615, 1985.

Siddiqui, et al., Isolation And Sequencing Of A cDNA Coding For The Human DF3 Breast Carcinoma–Associated Antigen, Proc. Natl. Acad. Sci. USA 85:2320–2323, 1988.

Sloan, et al., Distribution Of Epithelial Membrane Antigen In Normal And Neoplastic Tissues And Its Value In Diagnostic Tumor Pathology, Cancer 47:1786–1795, 1981.

Swallow, et al., The Human Tumour–Associated Epithelial Mucins Are Coded By An Expressed Hypervariable Gene Locus PUM, Nature 328:82–84, 1987.

Tondini, et al., Comparison of CA15-3 And Carcinoembryonic Antigen In Monitoring The Clinical Course Of Patients With Metastatic Breast Cancer, 48:4107–4122, 1988.

Xing et al., Synthetic Peptides Reactive with Anti–Human Mil Fat Globule Membrane Monoclonal Antibodies, Cancer Research 50:89–96, 1990.

Harris et al., Therapeutic Antibodies—The Coming of Age, TIBTECH 11:42–46, 1993.

MAb DF3-P

MAb DF3

MAb DF3-P

MAb DF3

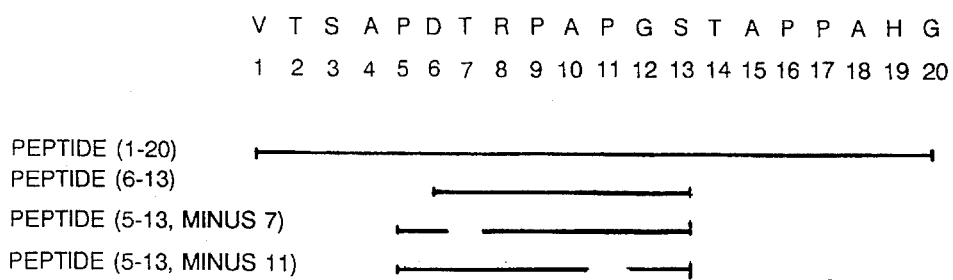
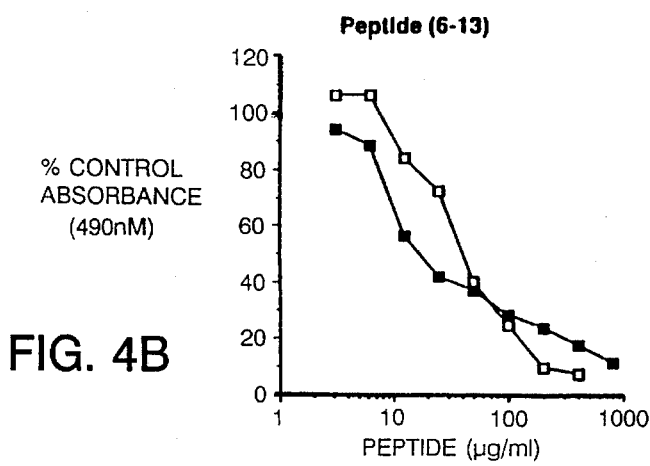
FIG. 4A
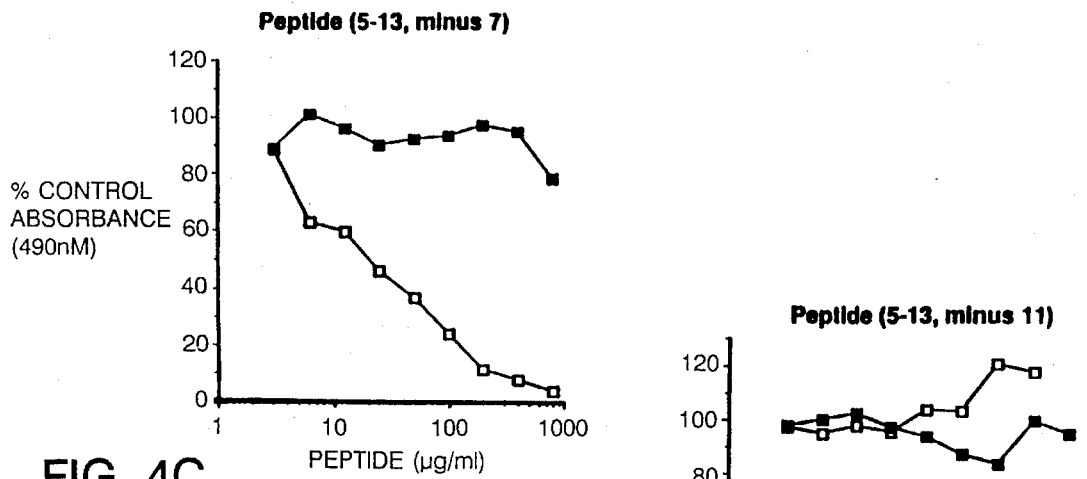
FIG. 4B
FIG. 4C
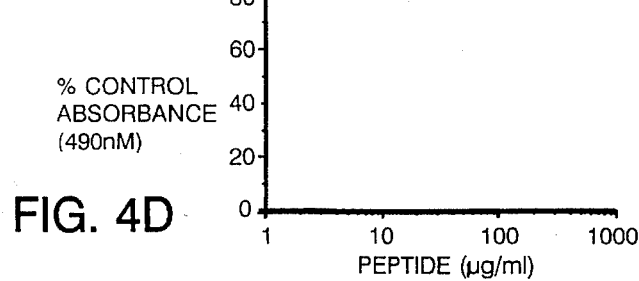
FIG. 4D

FIG. 6A   FIG. 6B
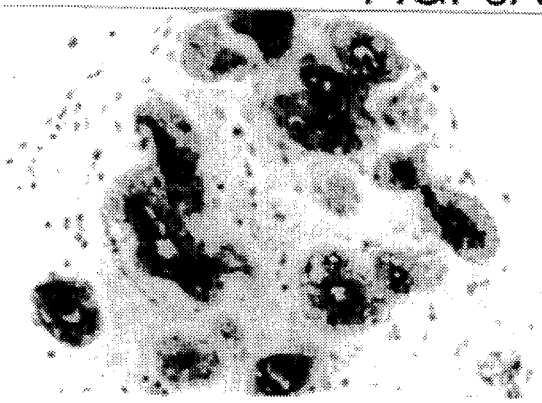
FIG. 6C   FIG. 6D

FIG. 6E   FIG. 6F
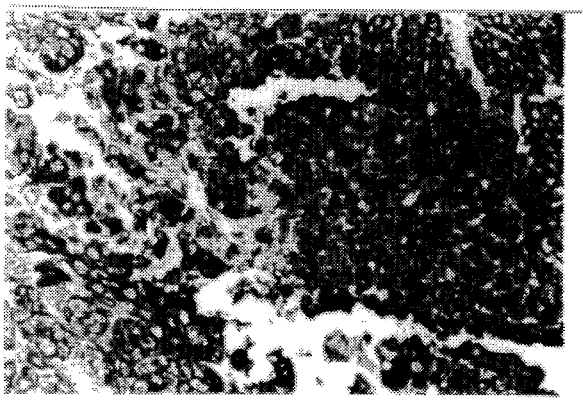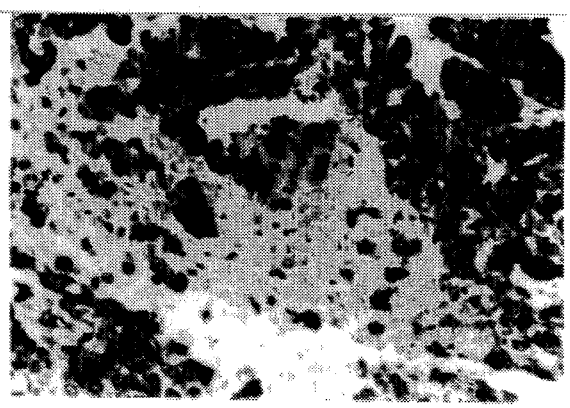
```
                        MAb DF3-P
                    ┌─────────────┐
V──H──P─D─T─R─P─A─P─G─S─T──H──G
1     5 6 7 8 9 10 11 12 13 14      20
            └───────────────┘
                 MAb DF3
```
FIG. 7

ANTIBODIES SPECIFIC FOR THE DF3 CARCINOMA ASSOCIATED ANTIGEN

This is a continuation of application Ser. No. 07/868,352, filed Apr. 13, 1992, now abandoned.

BACKGROUND OF THE INVENTION

The field of the invention is cancer-specific antigens.

Individuals with cancer frequently exhibit elevated levels of circulating antigens which are associated with that cancer. Such is the case in women with breast carcinoma. A monoclonal antibody (MAb) was prepared against a membrane-enriched extract of a human breast carcinoma metastatic to liver (Kufe et al., 1984, Hybridoma 3:223–232). The antibody was specific for what was termed DF3 antigen, a human breast carcinoma-associated antigen that is a collection of closely related, high molecular weight glycoproteins having the common property that they react with anti-DF3 antibodies. DF3 antigen is also described in U.S. Pat. No. 4,963,484 and in U.S. patent application Ser. No. 174,838, (now abandoned) both of which are herein incorporated by reference. DF3 antigen is detectable on the apical borders of normal secretory mammary epithelial cells and in the cytosol of less differentiated malignant breast cells (Kufe et al., 1984, Hybridoma 3:223–232). This apical and cytoplasmic staining pattern has also been described for MAbs prepared against human milk fat globule membranes (HMFGM) and breast carcinoma cell lines (Arklie et al., 1981, Int. J. Cancer 28:23–29; Hilkens et al., 1984, Int. J. Cancer 34:197–206; Sloane et al., 1981, Cancer 47:1786–1795; Croghan et al., 1983, Cancer Res. 43:4980–4988). Because DF3 antigen is detectable at elevated levels in the plasma of women with metastatic breast cancer, it has been used to monitor clinical course (Hayes et al., 1986, J. Clin. Oncol. 4:1542–1550; Tondini et al., 1988, Cancer Res. 8:4107–4122; Perey et al., 1990, Br. J. Cancer 62:668–670). Expression of this antigen has also been correlated with the degree of breast tumor differentiation and estrogen receptor status (Lundy et al., 1985, Br. Cancer Res. Treat. 5:269–276).

The finding that expression of DF3 in breast carcinoma cells and human milk is heterogenous suggested the possibility of a genetic polymorphism (Sekine et al., 1985, J. Immunol. 135:3610; Hilkens et al., 1989, Cancer Res. 49:786; Karlsson et al., 1983, Ann. Hum. Genet. 47:263). Indeed, studies in family members demonstrated that the electrophoretic heterogeneity of DF3 antigen is determined by codominant expression of multiple alleles at a single locus (Hayes et al., 1988, Blood 71:436). Sequence analysis of cDNA clones coding for this protein revealed highly conserved (G+C)-rich 60 base-pair tandem repeats (Swallow et al., 1987, Nature 328:82; Siddiqui et al., 1988, Proc. Natl. Acad. Sci. USA 85:2320; Gendler et al., 1988, J. Biol. Chem. 263:12820). These repeats code for epitopes recognized by MAb DF3, as well as other MAbs such as one termed SM-3 (Burchell et al., 1987, Cancer Res. 47:5476), prepared against the intact glycoprotein and the unglycosylated protein core (Siddiqui et al., 1988, Proc. Natl. Acad. Sci. USA 85:2320; Gendler et al., 1988, J. Biol. Chem. 263:12820; Burchell et al., 1987, Cancer Res. 47:5476). Moreover, these antibodies react with certain synthetic peptides prepared according to the in-frame sequence of the tandem repeat (Gendler et al., 1988, J. Biol. Chem. 263:12820; Abe and Kufe, 1989, Cancer Res. 49:2834).

SUMMARY OF THE INVENTION

A new monoclonal antibody has been discovered which binds to an epitope on DF3 antigen. The monoclonal antibody of the invention binds preferentially to unglycosylated, deglycosylated or immature DF3 antigen, or fragments thereof, rather than to the mature form of DF3 antigen that is expressed on the surface of cells in malignant mammary epithelium. Unglycosylated DF3 antigen is defined as a DF3 polypeptide that is free of any covalently attached carbohydrate moieties. A DF3 polypeptide is a polypeptide containing at least one copy of the 20 amino acid residue repetitive domain VTSAPDTRPAPGSTAPPAHG (SEQ ID No:1). Deglycosylated DF3 antigen is defined as a DF3 polypeptide which is partially glycosylated but which does not contain the same full contingent of carbohydrate moieties as the mature DF3 antigen expressed on the cell surface. Immature DF3 antigen is defined as a protein or glycoprotein containing the DF3 polypeptide, and which binds to the MAb of the invention with an affinity that is higher than that with which it binds to MAb DF3. Unglycosylated, deglycosylated and immature DF3 antigens contain the repetitive domain of DF3 polypeptide and are believed to be present in the cytoplasm and, in certain circumstances, the cell membrane, of breast cancer cells.

The invention features a MAb which binds preferentially to unglycosylated DF3 antigen, compared to mature DF3 antigen. By preferential binding is meant that the MAb has a significantly higher affinity for unglycosylated DF3 antigen than for the fully glycosylated mature DF3 antigen. Preferably, the MAb of the invention binds to unglycosylated DF3 antigen with an affinity that is at least 10 times higher (more preferably at least 50 times higher, and most preferably at least 100 times higher) than the affinity with which it binds to mature DF3 antigen.

The MAb of the invention preferably binds to an epitope on the repetitive domain of unglycosylated DF3 antigen, which epitope is contained within a portion of a peptide termed peptide(1-20) [which has the sequence VTSAPDTRPAPGSTAPPAHG (SEQ ID No:1)]. Preferably the MAb binds an epitope on unglycosylated DF3 antigen which is contained within a portion of a peptide termed peptide(6-13): DTRPAPGS (SEQ ID No:2), or peptide(7-13): TRPAPGS (SEQ ID No:3). More preferably the MAb binds to DRPAPGS (SEQ ID No:4) which is peptide(6-13) minus the threonine at position 7, and most preferably, the MAb binds to peptide(8-12), with the amino acid sequence RPAPG (SEQ ID No:5). Peptide(1-20) is a synthetic peptide containing 20 amino acids that encompass the MAb DF3 binding site of DF3 antigen. The amino acids are numbered 1 to 20 from the amino to the carboxy terminus of the peptide. Peptide(6-13) is a synthetic peptide the sequence of which represents a subset of the amino acids in peptide(1-20) (i.e., amino acids 6 to 13 of peptide(1-20), wherein amino acid 6 is at the amino acid terminus and amino acid 13 is at the carboxy terminus of peptide(6-13). The sequence RPAPG begins at amino acid number 8 of peptide(1-20).

In yet other preferred embodiments, the MAb of the invention reacts with a component of the cytoplasm of human carcinoma cells. The antibody specifically binds to a formalin-fixed breast tissue section containing infiltrating ductal carcinoma cells, but the MAb does not bind to a significant extent to a breast tissue section consisting entirely of normal cells (i.e., the MAb selectively binds to the cancer cell-containing sample, and not to the sample containing only normal cells). The MAb also is capable of binding to the cell membranes of certain human breast cancer cell lines, including cell lines ZR-75-1 and MCF-7. Most preferably, the antibody is produced by the hybridoma DF3-P, which is available from the American Type Culture Collection (ATCC Accession No. HB 11017). The MAb of the invention is also capable of binding to unglycosylated DF3 antigen with the same or higher affinity (preferably at least 10 times higher) with which DF3-P MAb binds to the unglycosylated antigen.

The invention also features a method of detecting unglycosylated, deglycosylated or immature DF3 antigen in a biological sample such as human breast tissue, other cancer tissue, blood, serum or urine. The method involves incubating the sample with an aliquot of the MAb and detecting the formation of an immune complex using, for example, an ELISA (enzyme-linked immunosorbent assay), the complex consisting of the antibody and a component of the sample. Formation of such an immune complex is indicative of the presence of unglycosylated, deglycosylated or immature DF3 antigen in the sample. More preferably, the method further includes the steps of providing a control sample containing a standard amount of unglycosylated DF3 antigen, incubating the control sample with the MAb, and comparing the amount of immune complex formation in the biological sample to the amount of immune complex formation in the control sample.

The invention also includes a method for diagnosing cancer (e.g., breast cancer, lung cancer, or ovarian cancer) in a human involving incubating a biological sample, for example a fixed tissue section, with the MAb of the invention which has attached to it a detectable label, and detecting the label bound to the sample, wherein detection of an amount of label significantly above background levels is an indication that the patient has cancer in that tissue.

The invention also features an immunotoxin in which the MAb of the invention, or an antigen-binding fragment thereof, is linked to a cytotoxic agent. The cytotoxic agent is preferably chemically conjugated to the MAb or fragment thereof, or alternatively is a polypeptide which is attached to the MAb by means of a peptide bond and is produced by genetic engineering techniques.

This immunotoxin may be used to treat a human patient with a breast or other DF3-P-antigen-expressing tumor, by administering the immunotoxin to the patient, e.g., by intravenous injection or another suitable route.

Also included in the invention is an imaging agent consisting of the MAb of the invention, or an antigen-binding fragment thereof, which is linked to a detectable label, for example, a radionuclide. This imaging agent can be used for detecting tumors in situ by administering the imaging agent to a patient suspected of having a tumor (e.g., a breast, lung or ovarian tumor). Detection of the detectable label (preferably a radionuclide which is detected by radioimaging) bound to a tissue in the patient is indicative that the patient has a tumor at that site.

The invention also features an immunoassay kit which contains the MAb of the invention, reagents for detection of binding of the MAb to DF3 antigen, and instructions for using the kit.

Also included in the invention is a method of treating a human patient with breast, lung, ovarian, or other cancer involving administering to the patient the MAb of the invention, wherein the MAb is coupled (e.g., by chemical means) to a radionuclide. The radionuclide is preferably one which is capable of killing a cell with which it comes in contact: for example, an α-particle emitter such as $^{90}Y$ (Yttrium). The MAb will bind to a cell expressing the MAb-specific epitope, and because it is so coupled to the radionuclide, the radionuclide will contact the cell and effect its killing.

The invention also includes a vaccine comprising a molecule consisting essentially of the epitope RPAPG, (SEQ ID No:5) in a physiologically acceptable carrier, and a method of immunizing a person by introducing an immunizing amount of the vaccine into the person. Such a molecule may also include additional amino acid sequence or other moieties, e.g., to promote the stability or immunogenicity of the vaccine.

DETAILED DESCRIPTION

The drawings are first described.

The Drawings FIG. 1A is an immunoblot analysis showing reactivity of MAb DF3-P. Lane 1: MAb affinity purified DF3 antigen from milk. Lane 2: extract from ZR-75-1 cells. Lane 3: MAb DF3 affinity purified DF3 antigen from ZR-75-1 culture supernatant. Lane 4: MAb DF3-P affinity purified DF3/β-galactosidase fusion protein. The proteins were subjected to electrophoresis in 3–10% polyacrylamide gradient gels, transferred to nitrocellulose paper, and analyzed for reactivity with MAbs DF3 and DF3-P.

FIG. 1B is an immunoblot analysis showing reactivity of MAb DF3 to each of the antigens tested in FIG. 1A. Lanes are as described for FIG. 1A.

FIG. 2A is an immunoblot analysis showing reactivity of MAb DF3-P with MAb-DF3-affinity-purified and enzymatically deglycosylated DF3 antigen from ZR-75-1 tissue culture supernatant. Each lane is as described for FIG. 2A. Lane 1: undigested DF3 antigen. Lane 2: antigen treated with 15 mU neuraminidase for 2 h. Lane 3: antigen treated with neuraminidase for 2 h and 2 mU O-glycanase for 2 h. Lane 4: antigen treated with neuraminidase for 2 h and O-glycanase for 10 h.

FIG. 2B is an immunoblot analysis showing reactivity of MAb DF3 with MAb-DF3-affinity-purified and enzymatically deglycosylated DF3 antigen from ZR-75-1 tissue culture supernatant. Each lane is as described for FIG. 2A.

FIG. 3 shows the competitive effects of synthetic peptides on the binding of MAb DF3-P to peptide(1-20). Peroxidase-conjugated MAb DF3-P was preincubated with the indicated concentrations of peptide(1-10) (Δ), peptide(11-20) (O), peptide (11-20-10) (o) and peptide(1-20) (□) for 1 h at room temperature and then added to peptide(1-20)-coated wells. After an additional 1 h at room temperature, the wells were washed and developed with OPD.

FIG. 4A is a schematic representation of the 20 amino acid tandem repeat sequence and the synthetic peptides used in the compeition assays illustrated in FIGS. 4B–4D, which assays permit epitope mapping of the DF3-P and DF3 binding sites.

FIG. 4B is a graph illustrating the results of preincubating peroxidase-conjugated MAb DF3-P (□) and MAb DF3 (■) with the indicated concentration of peptide(6-13), followed by addition to peptide (1-20)-coated wells were then washed and developed with OPD.

FIG. 4C is a graph illustrating the results of preincubating peroxidase-conjugated MAb DF3-P (□) and MAb DF3 (■) with the indicated concentration of peptide(5-13, minus 7), followed by addition to peptide(1-20)-coated wells; the wells were then washed and developed with OPD.

FIG. 4D is a graph illustrating the results of preincubating peroxidase-conjugated MAb DF3-P (□) and MAb DF3 (■) with the indicated concentration of peptide(5-13, minus 11), followed by addition to peptide(1-20)-coated wells; the wells were then washed and developed with OPD.

Figure 5:
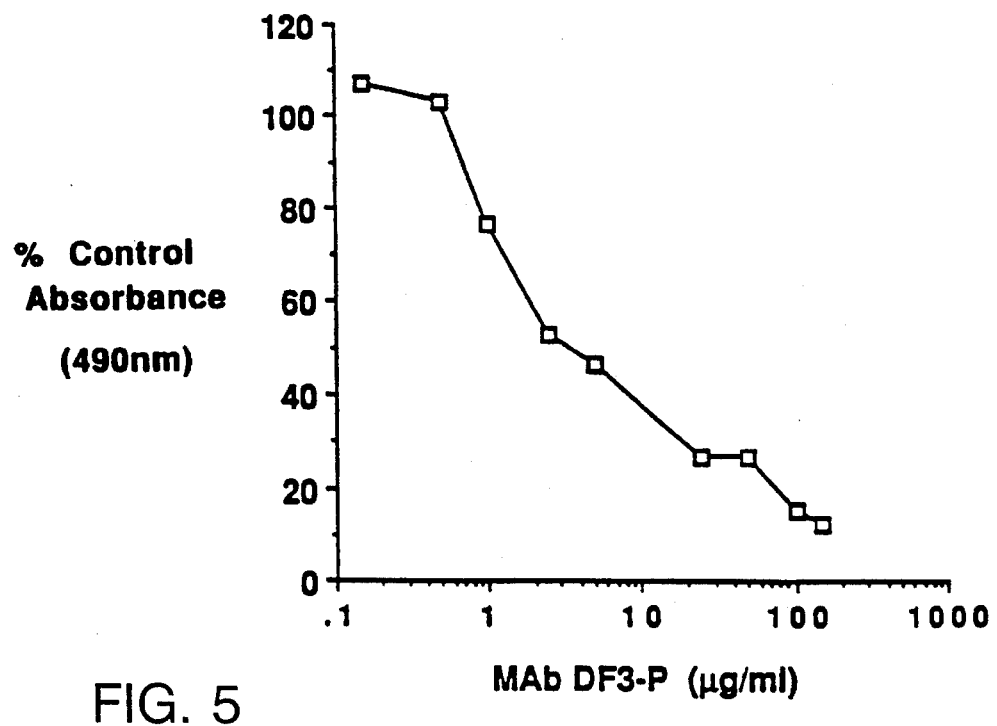

FIG. 5 is a graph showing inhibition of peroxidase-conjugated MAb DF3 binding to peptide(1-20) by MAb DF3-P. Wells coated with peptide(1-20) were preincubated with the indicated concentrations of nonconjugated MAb DF3-P for 4 h at room temperature. After washing, preoxidase-conjugated MAb DF3 was then added for 1 h and reactivity determined by development with OPD.

FIG. 6A is a photograph showing reactivity of MAb DF3 with a formalin-fixed, paraffin-imbedded tissue section from a reduction mammoplasty. The tissue section in this figure and in each of FIGS. 6B–6F was stained with the appropriate MAb using the immunoperoxidase technique.

FIG. 6B is a photograph showing reactivity of MAb DF3-P with a formalin-fixed, paraffin-imbedded tissue section from a reduction mammoplasty.

FIG. 6C is a photograph showing reactivity of MAb DF3 with a formalin-fixed, paraffin-imbedded tissue section from an infiltrating ductal carcinoma. The arrows highlight normal ducts (adjacent to tumor) which stain with MAb DF3, but not with MAb DF3-P (compare to FIG. 6D).

FIG. 6A is a photograph showing reactivity of MAb DF3 with a formalin-fixed, paraffin-imbedded tissue section from a reduction mammoplasty. The tissue section in this figure and in each of FIGS. 6B–6F was stained with the appropriate MAb using the immunoperoxidase technique.

FIG. 6B is a photograph showing reactivity of MAb DF3-P with a formalin-fixed, paraffin-imbedded tissue section from a rreduction mammoplasty.

FIG. 6C is a photograph showing reactivity of MAb DF3 with a formalin-fixed, paraffin-imbedded tissue section from an infiltrating ductal carcinoma. The arrows highlight normal ducts (adjacent to tumor) which stain with MAb DF3, but not with MAb DF3-P (compare to FIG. 6D).

FIG. 6D is a photograph showing reactivity of MAb DF3-P with a formalin-fixed, paraffin-imbedded tissue section from the same infiltrating ductal carcinoma as shown in FIG. 6C. The arrows highlight normal ducts (adjacent to tumor) which stain with MAb DF3, but not with MAb DF3-P (compare to FIG. 6C).

FIG. 6E is a photograph showing reactivity of MAb DF3 with formalin-fixed, paraffin-imbedded tissue section from a second infiltrating ductal carcinoma.

FIG. 6F is a photograph showing reactivity of MAb DF3-P with a formalin-fixed, paraffin-imbedded tissue section from the same infiltrating ductal carcinoma as shown in FIG. 6E.

EXPERIMENTAL DATA

Materials & Methods

Purification of a DF3/β-galactosidase fusion protein.

Cultures of *E. coli* strain Y 1089, infected with λgt11 phage containing the DF3 antigen tandem repeat sequence (309 base pairs), were grown in LB medium at 32° C. (Siddiqui et al., 1988, Proc. Natl. Acad. Sci. U.S.A, 85:2320–2323). Expression of the fusion protein was induced by addition of 10 mM isopropylthio-β D-galactoside (IPTG). After induction for 1–2 h, bacteria were harvested by centrifugation, resuspended in TEP buffer (100 mM Tris-HCl, pH 7.4, containing 10 mM EDTA and 1 mM phenylmethylsulfonyl fluoride (PMSF)), frozen at −70° C. and then lysed by sonication for 10–15 min. After centrifugation at 10,000 rpm for 10 min, the supernatant was collected and applied to a Sephacryl S-300 column. Fractions that contained the DF3/β-galactosidase fusion protein, as determined by Western blot analysis with MAb DF3, were pooled, applied to a MAb DF3 affinity column and eluted with 3M $MgCl_2$.

Immunization and Hybridoma Production

Eight-week-old BALB/c mice were immunized by intraperitoneal and then intravenous injection of the DF3/β-galactosidase fusion protein. Hybridomas were prepared by fusion of immune spleenocytes with the murine NS 1 myeloma cell line (Kufe et al., 1984, Hybridoma, 3:223–232) and screened by enzyme-linked immuno-sorbent assay (ELISA). Immulon II plates (Fisher Scientific, Pittsburgh, Pa.) were coated with 5 μg/ml of synthetic peptide (VTSAPDTRPAPGSTAPPAHG (SEQ ID No:1); peptide(1-20)) in 0.1M borate buffer, pH 8.0, overnight at 37° C. The plates were incubated with blocking buffer (1% BSA in 0.018M phosphate-buffered saline (PBS), 0.1% Tween 20) for 1 h. The wells were washed, incubated with hybridoma supernatant (50 μl) at 37° C. for 2 h, washed again, incubated with a peroxidase-conjugated goat antibody against mouse IgG (Boehringer Mannheim) for 1 h at room temperature and then developed with 5.5 μM O-phenylene diamine (OPD; Sigma) in 0.1M citrate buffer (pH 4.5) containing 0.012% hydrogen peroxide. Reactivity was monitored at 490 nm with a Minireader (Dynatech Laboratory, Alexandria, Va). Isotyping was performed with a Bio-Rad isotyping Kit (Richmond, Calif).

Competition Assays.

Synthetic peptides were serially diluted in PBS, incubated with peroxidase-conjugated MAb in PBS containing 0.1% Tween 20 for 1 h, and then added to peptide(1-20) coated wells for 1 h at room temperature. Alternatively, saturating concentrations of non-conjugated MAb in Tween buffer (0.1% Tween 20, 0.5M NaCl, 0.05M potassium phosphate, pH 8.0)/0.5% BSA were added to peptide(1-20) coated wells for 4 h at room temperature. Plates were washed 4× with PBS/0.1% Tween 20. Peroxidase-conjugated MAb in Tween buffer/0.5% BSA was then added and incubated for 1 h. The plates were washed 5× with PBS/0.1% Tween 20 and developed with OPD.

Enzymatic deglycosylation of DF3 antigen.

Affinity purified DF3 antigen (50 μg) from ZR 75-1 cell culture supernatant (Abe and Kufe, 1987, J. Immunol., 139:257–261; Sekine et al., 1985, J. Immunol., 135:2610–3516) was lyophilized, denatured by boiling for 5 min in 7 μl 0.5% SDS, 0.1M β-mercaptoethanol, and incubated with 15 mU neuraminidase (Sigma) in 21 μl 50 mM sodium acetate, pH 5.0. After 2 h, the pH was adjusted to 6.5 with 20 mM $Na_2HPO_4$, and then 2 mU endo-α-N-acetyl-galactosaminidase (O-glycanase™, Genzyme, Boston, Mass.) was added for 2–10 h. Incubations were performed at 37° C. in the presence of 1 mM PMSF, 1 μM leupeptin and 1 μM pepstatin, 0.3 μM protinin, 100 μM $Na_2EDTA$.

Results

Figure 1A:
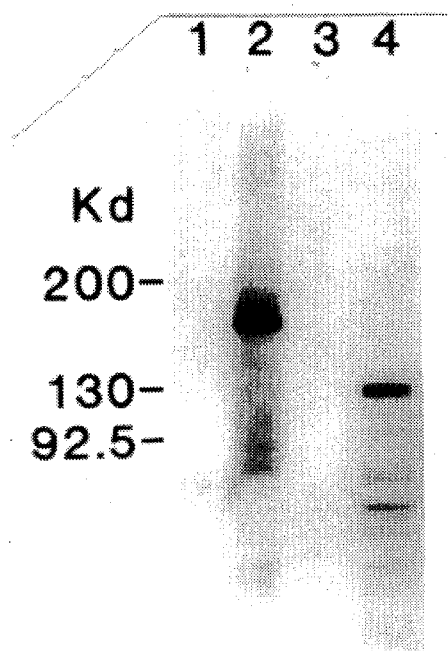
Figure 1B:
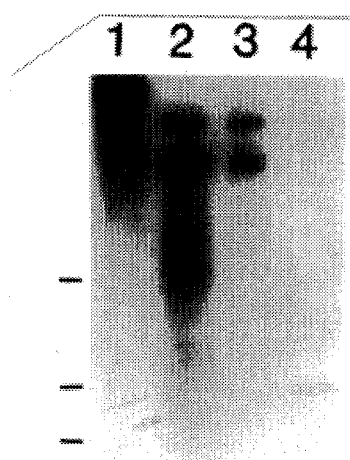

Immunization with the DF3/β-galactosidase fusion protein resulted in the production of an IgG2a MAb, designated DF3-P, which reacted by ELISA with peptide(1-20). This antibody was subjected to further characterization by immunoblot analysis. There was little if any reactivity of MAb DF3-P with DF3 antigen purified from HMFGM by MAb DF3 affinity chromatography (Abe and Kufe, 1987, J. Immunol., 139:257–261; Sekine et al., 1985, J. Immunol., 135:3610–3516) (FIG. 1A, Lane 1). In contrast, MAb DF3-P did react with extracts of ZR-75-1 breast carcinoma cells (FIG. 1A, Lane 2). This reactivity was predominantly against a protein of approximately 170 Kd (FIG. 1A, Lane 2). While these findings indicated that MAb DF3-P reacts with a ZR-75-1 cell antigen, there was no detectable binding of MAb DF3-P to DF3 antigen purified by MAb DF3 affinity chromatography from ZR-75-1 culture supernatants (FIG. 1A, Lane 3). Nonetheless, MAb DF3-P did bind to the 130 Kd DF3/β-galactosidase fusion protein and several smaller fragments present in bacterial extracts (FIG. 1A, Lane 4). These findings were compared to those obtained with MAb DF3. This antibody reacted with DF3 antigen purified from HMFGM and ZR-75-1 culture supernatant (FIG. 1B, Lanes 1 and 3). Moreover, while MAb DF3 also reacted with ZR-75-1 cell extract, the pattern of reactivity was distinct from that obtained with MAb DF3-P (FIG. 1B, Lane 2). MAb DF3 also reacted with the DF3/β-galactosidase fusion protein, although the intensity of this signal was less than that found for MAb DF3-P (FIG. 1B, Lane 4).

Figure 2A:
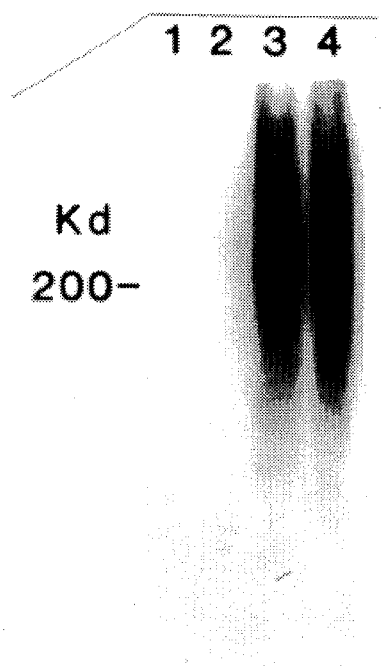
Figure 2B:

Previous studies have demonstrated that the DF3 core protein has an apparent Mr of approximately 170 Kd (Abe and Kufe, 1989, Cancer Res., 49:2834–2839). The findings with MAb DF3-P thus suggested that this antibody might exhibit selective reactivity with a precursor of the DF3 glycoprotein. In order to address this issue, DF3 antigen purified by MAb DF3 affinity chromatography from ZR-75-1 culture supernatant was digested with neuraminidase and O-glycanase. There was no detectable reactivity of MAb DF3-P with undigested DF3 antigen (FIG. 2A, Lane 1) or after treatment with neuraminidase (FIG. 2A, Lane 2). In contrast, MAb DF3-P reactivity was apparent after treatment of DF3 antigen with both neuraminidase and O-glycanase. Indeed, similar patterns of broad reactivity were obtained after exposure of the purified antigen to these enzymes for 2 h or 10 h (FIG. 2A, Lanes 3 and 4). These findings were distinct from those obtained with MAb DF3. While binding of this antibody to DF3 antigen (FIG. 2B, Lane 1) was undetectable after treatment with neuraminidase alone (FIG. 2B, Lane 2), exposure to both neuraminidase and O-glycanase was associated with the detection of several higher molecular weight species than those identified with MAb DF3-P (FIG. 2B, Lanes 3 and 4). Taken together, these results indicated that MAb DF3-P reacts with the DF3 peptide and not with the mature glycoprotein, while MAb DF3 reacts principally with the glycosylated protein.

Figure 3:
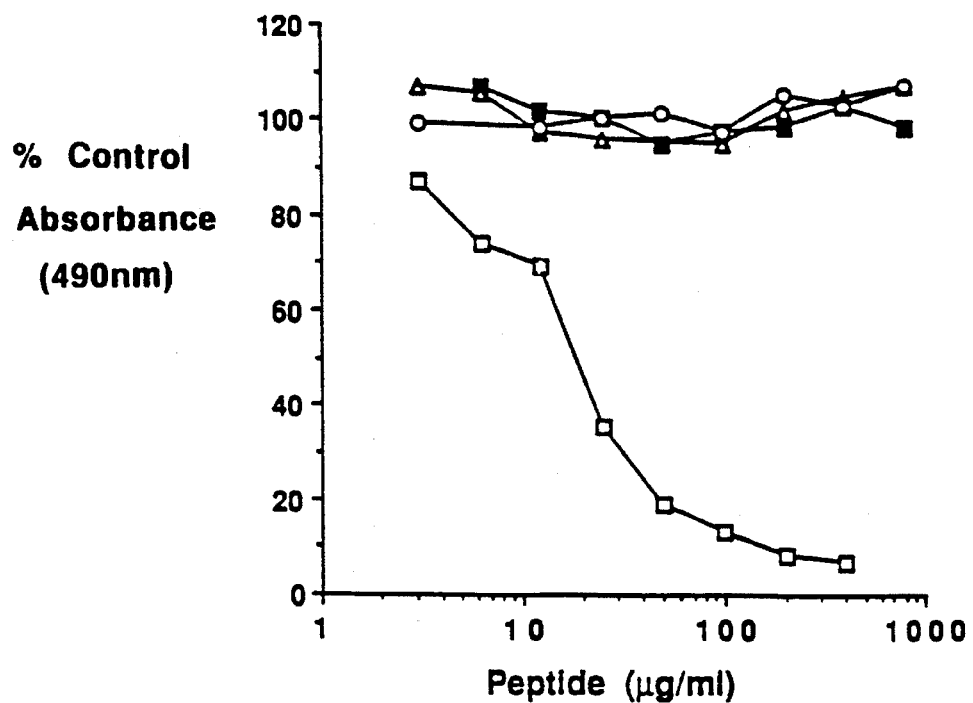

Further characterization of MAb DF3-P reactivity was approached by epitope mapping. The demonstration that MAb DF3-P binds to peptide(1-20) indicated that the reactive epitope is present within this repetitive domain. In order to confirm this hypothesis, smaller synthetic peptides representing portions of that domain were used to compete for MAb DF3-P binding to peptide(1-20). Decamer(1-10) (VTSAPDTRPA; SEQ ID No:6) and decamer(11-20) (PGSTAPPAHG; SEQ ID No:7) had no detectable competitive effect at concentrations of up to 800 μg/ml (FIG. 3). Moreover, the dodecamer(11-20-10) had no effect on binding of MAb DF3-P to peptide(1-20) (FIG. 3). Taken together with the finding that peptide(1-20) completely blocks MAb DF3-P binding in this assay (FIG. 3), these results indicated that the epitope for this antibody resides at or near amino acids 10 and 11 (FIG. 4A). In addition, the finding that similar results were obtained with MAb DF3 indicated that these antibodies may bind to the same region.

In order to more precisely map the MAb DF3-P epitope, additional competition studies were performed with various octamers spanning amino acids 10 and 11 (FIG. 4). Peptide(6-13) was effective in blocking binding of both MAb DF3-P and MAb DF3 to peptide(1-20) (FIG. 4B). In contrast, a peptide spanning amino acids 5 to 13, but without the threonine at position 7, effectively blocked binding of MAb DF3-P and not MAb DF3 (FIG. 4C). These results indicate that while amino acid 7 is required for MAb DF3 binding, this residue is not involved in the epitope defined by MAb DF3-P. Moreover, a peptide spanning amino acids 5 to 13 without the proline at position 11 had no detectable effect on binding of either MAb DF3-P or DF3 (FIG. 4C). A peptide spanning amino acids 6–14, but without the serine at position 13, blocked MAb DF3-P binding and had limited effects on reactivity of MAb DF3 with peptide (1-20). These findings indicate that the MAb DF3-P and DF3 epitopes both involve amino acid 11 and therefore are overlapping. This issue was further addressed by determining whether these antibodies compete for binding to peptide(1-20). Indeed, the finding that MAb DF3-P blocks binding of peroxidase-conjugated MAb DF3 to this peptide (FIG. 5) provides further support for the similarity of the DF3-P and DF3 epitopes. Previous studies have demonstrated that MAb DF3 reacts with the apical borders of normal mammary epithelium (Kufe et al., 1984, Hybridoma, 3:223–232). This characteristic apical staining pattern was detectable with MAb DF3 in formalin-fixed paraffin-embedded normal mammary tissue obtained from a reduction mammoplasty (FIG. 6A). In contrast, there was little if any detectable staining of this tissue with MAb DF3-P (FIG. 6B). Similar results were obtained with two separate mammoplasty specimens. Other studies were performed on infiltrating ductal carcinomas of the breast. Patterns of MAb DF3 (FIGS. 6C and E) were different from those obtained with MAb DF3-P (FIG. 6D and F). MAb DF3 staining was both apical and cytoplasmic, while reactivity with MAb DF3-P was predominantly in the cytoplasm. Sections of normal ducts adjacent to tumor stained with MAb DF3, but not MAb DF3-P (FIG. 6C and D; arrows). Moreover, certain sections of the tumor stained more intensely with MAb DF3-P than MAb DF3. Of nine infiltrating ductal carcinomas and one ductal in situ carcinoma stained with MAb DF3-P, all had detectable reactivity in the majority of tumor cells and little if any staining of normal components.

DF3 antigen and related members of this family of high molecular weight glycoproteins are aberrantly expressed in human breast carcinomas, as well as certain other types of carcinomas. These glycoproteins are detectable at high levels in the cytoplasm of transformed mammary epithelium. Pulse-chase labeling and immunoprecipitation experiments have confirmed the synthesis of core proteins ranging in size from 160 to 220 Kd (Abe and Kufe, 1989, Cancer Res. 49:2834–2839; Hilkens and Buijs, 1988, J. Biol. Chem., 263:4215–4222). The mature glycoproteins are generated through several lower molecular weight precursors. In this context, maturation appears to involve proteolytic cleavage of the protein backbone in the endoplasmic reticulum and addition of O-linked glycans (Hilkens and Buijs, 1988, J. Biol. Chem., 263:4215–4222). While extensive O-glycosylation is primarily responsible for the increase in apparent molecular weight of the mature glycoprotein, other findings also support the presence of N-linked glycans (Abe and Kufe, 1989, Cancer Res. 49:2834–2839; Hilkens and Buijs, 1988, J. Biol. Chem., 263:4215–4222). Recent studies have demonstrated that the carbohydrate structure of purified DF3 glycoprotein from malignant breast cells is different from that obtained for the related antigen in human milk (Hull et al., 1989, Cancer Commun., 1:261–267). The major carbohydrate component of the DF3 glycoprotein from BT-20 breast carcinoma cells is the Thomsen-Friedenreich antigen (Galβ1,3GalNac), while this structure is undetectable in the related milk glycoprotein (Hull et al., 1989, Cancer Commun., 1:261–267). These findings suggest that differential glycosylation of the protein core may provide an opportunity to prepare MAbs selectively reactive with antigen produced by transformed cells.

Preliminary data obtained with the breast cancer cell lines ZR-75-1 and MCF-7 indicate that the immature DF3 antigen is expressed on the surfaces of breast cancer cells, although in lesser amounts than mature DF3 antigen. In addition, immature DF3 antigen has been found to be associated with certain lung cancer and ovarian cancer cells, indicating that it is a marker for these types of cancers as well as breast cancer (data not shown).

The invention involves an antibody which binds to an epitope on the DF3 protein, but has little if any reactivity with the mature glycoprotein. Importantly, the DF3-P epitope is similar to but distinct from that defined by MAb DF3. While the DF3 and DF3-P epitopes both reside within amino acids 6 to 13 and involve the proline residue at position 11 (FIG. 7), MAb DF3 reacts weakly with unglycosylated peptide, and its binding is significantly enhanced in the presence of carbohydrate moieties (Abe and Kufe, 1987, J. Immunol. 139:257; Siddiqui et al., 1988, Proc. Natl. Acad. Sci. USA 85:2320; Abe and Kufe, 1989, Cancer Res. 49:2834), presumably by glycosylation at the threonine at position 7 and/or the serine at position 13. In contrast, this glycosylation appears to inhibit binding of MAb DF3-P. Thus MAb DF3-P can bind to both the unglycosylated DF3 epitope (amino acids 6-13) and to amino acids 8-12 which lack the glycosylation sites (residues 7 and 13) of the DF3 epitope. The DF3-P epitope is distinct from the epitope to which another MAb (SM-3) has been shown to bind, in that the SM-3 epitope is defined by amino acids 5-9 of peptide(1-20), containing the sequence PDTRP (SEQ ID No:8) (Burchell et al., 1989, Int. J. Cancer 44:691). A further distinction between the DF3-P and SM-3 epitopes is the fact that the DF3-P epitope is resistant to denaturation by formalin, whereas the SM-3 epitope is sensitive and denatures upon contact with formalin (Burchell et al., 1987, Cancer Res. 47:5476).

Other Embodiments

Other embodiments of the invention are within the claims set forth below and within the following discussion.

Hybridomas producing unglycosylated DF3 antigen-specific monoclonal antibodies may be prepared as described above by immunization of mice or other animals with extracts from breast carcinoma cells, with preparations of purified or semi-purified unglycosylated or deglycosylated DF3 antigen, or with fragments of unglycosylated or deglycosylated DF3 antigen, such as peptide(1-20), peptide(6-13), or peptide(8-12). The monoclonal antibodies so produced can be assayed and characterized using the procedures described above for MAb DF3-P. For example, binding to DF3 antigen, or fragments thereof, can be assessed by ELISA, Western blotting technology, competitive inhibition studies with peptide fragments, and the like. The DF3 antigen immunoassay of the invention can utilize any standard immunoassay procedure known to those who practice the art of immunoassays, including but not limited to ELISA, radioimmunoassay, fluoroimmunoassay, luminescent immunoassay, and competitive immunoassay. Where the immunoassay detects unglycosylated, deglycosylated, or immature DF3 antigen by sandwiching it between two or more antibody molecules, both antibody molecules can be specific for the same type of determinant on the antigen (there being at least two of such determinant type on each molecule of DF3 antigen), or can bind to different types of determinants on the antigen. Other assays could be based upon a non-sandwich format, such as a direct competition assay well known to those skilled in the art of immunoassays.

The immunoassay of the invention can be incorporated into an immunoassay kit. The kit can comprise a monoclonal antibody which binds preferentially to unglycosylated DF3 antigen; a means for detecting and measuring such binding; and instructions for using the kit. The kit can utilize any appropriate type of immunoassay as discussed above. For example, the kit may include reagents for an immunoassay, wherein a sample from a patient (e.g., a fixed tissue specimen, or a bodily fluid such as blood, serum or urine) is first reacted with a MAb that binds preferentially to unglycosylated DF3, and a second antibody is then added which is capable of binding to the Fc portion of the first antibody, and which has bound to it an indicator enzyme capable of reacting with a substrate. Unbound antibody is removed from the mixture and the substrate with which the enzyme reacts is then added. The substrate is one which undergoes a detectable and measurable change following reaction with the enzyme. Thus, the degree of change in the substrate is a direct measure of the amount of DF3 antigen in the sample.

The immunotoxin of the invention can be prepared by chemically conjugating a monoclonal antibody specific for unglycosylated DF3 antigen to any of a number of known toxic entities, using techniques well known to those of ordinary skill in the art of immunotoxin production. A typical way of conjugating antibodies to protein toxins (including, for example, bacterial toxins such as diphtheria toxin or Pseudomonas exotoxin A, or plant toxins such as ricin) is by crosslinking through a disulfide bond (e.g., Chang et al., J. Biol. Chem. 252:1515–1522, 1977) or a heterobifunctional molecule (e.g., Cawley et al., Cell 22:563–570, 1980). See also Stevens et al., U.S. Pat. No. 4,894,227. Alternatively, the immunotoxin can be prepared by expression of a hybrid DNA engineered to encode both the toxin (or a toxic portion thereof) and the antibody (or an DF3-binding portion thereof), using technology available to those of ordinary skill in the art of making such hybrids (see, e.g., Murphy, U.S. Pat. No. 4,675,382, and Chaudhary et al., Proc. Natl. Acad. Sci. USA 84:4538–4542, 1987; each of which is herein incorporated by reference). The DNA sequence encoding the DF3-binding portion of the immunotoxin would be based upon the variable light-chain ($V_L$) amino acid sequence and the variable heavy-chain ($V_H$) sequence of a DF3-specific antibody of the invention; using the method of Bird et al., Science 242:423–426, 1988, a DNA sequence encoding the $V_L$ joined to the $V_H$ by a linker peptide would be constructed and linked to a DNA sequence encoding the protein toxin (or a toxic portion thereof, as taught by, for example, Murphy U.S. Pat. No. 4,675,382). Such manipulations would be routine to one of ordinary skill in the art of genetic engineering, given the disclosures set forth herein. The resulting immunotoxin could be formulated for use as an anti-cancer agent, following procedures standard to the field of pharmacology.

The monoclonal antibody of the invention can alternatively be combined with a detectable label to produce an imaging agent useful for detecting and localizing DF3-expressing tumors in vivo. Methods of attaching such labels to antibodies are well known in the art, and can be readily accomplished without undue experimentation. The potential usefulness of such an agent can be assayed, for example, by implanting DF3-specific tumor cells into an immunocompromised host (such as a nude mouse) and determining whether or not the imaging agent of the invention detectably labels the tumor produced by such implanted cells.

The monoclonal antibody of the invention can also be combined with an α-emitting radionuclide, using methods well known to those in the art. Such a complex is capable of killing a cell with which it comes in contact. A patient with breast, lung, ovarian, or other cancer can be treated with the antibody complex by administering the complex, suspended in a physiologically acceptable carrier, to the patient intravenously, or by local injection at the tumor site. Tumor cells which express the epitope to which the MAb binds will be killed following contact with the radionuclide.

In yet another use of the invention, the epitope to which the monoclonal antibody binds can be useful as a vaccine to protect individuals from acquiring cancer, or to stimulate a cancer patient's immune system into producing antibodies that will target the cancerous cells. The epitope can be suspended in a physiologically acceptable carrier for inoculation into humans. Determining the appropriate dosage and mode of administration is within the abilities of one of ordinary skill in the art.

Deposit

Under the terms of the Budapest Treaty on the International Recognition of the Deposit of Microorganisms for the Purpose of Patent Procedure, deposit of hybridoma DF3-P has been made with the American Type Culture Collection (ATCC) of Rockville, Md., U.S.A, where the deposit was given ATCC Accession Number HB 11017, and a deposit date of Apr. 13, 1992.

Applicant's assignee, Dana Farber Cancer Institute, Inc., represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 C.F.R. 1.14 and 35 U.S.C. § 122. The deposited material will be maintained with all the care necessary to keep it viable and uncontaminated for a period of at least five years after the most recent request for the furnishing of a sample of the deposited material, and in any case, for a period of at least thirty (30) years after the date of deposit or for the enforceable life of the patent, whichever period is longer. Applicant's assignee acknowledges its duty to replace the deposit should the depository be unable to furnish a sample when requested due to the condition of the deposit.

What is claimed is:

1. A monoclonal antibody which binds preferentially to unglycosylated DF3 antigen, compared to mature DF3 antigen, said antibody being specific for an epitope within the following amino acid sequence: $T_7R_8P_9A_{10}P_{11}G_{12}S_{13}$ (SEQ ID NO:3), which epitope is stable to formalin treatment and includes a proline at position 11.

2. The antibody of claim 1, wherein said epitope is within the following amino acid sequence: $R_8P_9A_{10}P_{11}G_{12}$ (SEQ ID No:5).

3. The antibody of claim 1, wherein said antibody binds to unglycosylated DF3 antigen with at least ten times the affinity with which said antibody binds to mature DF3 antigen.

4. The antibody of claim 1, wherein said antibody binds to a peptide having the following amino acid sequence: $D_6R_8P_9A_{10}P_{11}G_{12}S_{13}$ (SEQ ID NO: 4).

5. The antibody of claim 1, wherein said antibody forms an immune complex with an antigen in the cytoplasm of human carcinoma cells.

6. The antibody of claim 1, wherein said antibody binds to the same epitope to which DF3-P monoclonal antibody produced by the hybridoma having ATCC Accession No. HB 11017 binds.

7. The antibody of claim 1, wherein said antibody is produced by the hybridoma DF3-P (ATCC Accession No. HB 11017).

8. The antibody of claim 1, wherein said antibody binds to said epitope on said unglycosylated antigen with the same or higher affinity with which DF3-P monoclonal antibody (ATCC Accession No. HB 11017) binds to said epitope on said unglycosylated antigen.

9. The antibody of claim 1, wherein said antibody binds to a breast tissue section comprising infiltrating ductal carcinoma cells, but not to a breast tissue section consisting entirely of normal cells.

10. A complex comprising the antibody of claim 1, or an antigen-binding fragment thereof, linked to a detectable label.

11. The complex of claim 10, wherein said label is a radionuclide.

12. An immunotoxin comprising the antibody of claim 1, or an antigen-binding fragment thereof, linked to a cytotoxic agent.

13. The immunotoxin of claim 12, wherein said cytotoxic agent is chemically conjugated to said antibody or said antigen-binding fragment.

14. The immunotoxin of claim 12, wherein said cytotoxic agent is a polypeptide, and said polypeptide is linked by a peptide bond to said antigen-binding fragment.

15. An immunoassay kit comprising the monoclonal antibody of claim 1 and instructions for using said kit.

16. An antigen-binding fragment of the antibody of claim 1.

17. An antigen-binding fragment of the antibody of claim 2.

18. An antigen-binding fragment of the antibody of claim 3.

19. An antigen-binding fragment of the antibody of claim 4.

20. An antigen-binding fragment of the antibody of claim 5.

21. An antigen-binding fragment of the antibody of claim 6.

22. An antigen-binding fragment of the antibody of claim 7.

23. An antigen-binding fragment of the antibody of claim 8.

24. An antigen-binding fragment of the antibody of claim 9.

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 20
        ( B ) TYPE: amino acid
        ( C ) STRANDEDNESS:
        ( D ) TOPOLOGY: linear ( x i ) SEQUENCE DESCRIPTION: SEQ ID NO: 1:

```
Val  Thr  Ser  Ala  Pro  Asp  Thr  Arg  Pro  Ala  Pro  Gly  Ser  Thr  Ala  Pro
 1                  5                        10                       15
Pro  Ala  His  Gly
               20
```

( 2 ) INFORMATION FOR SEQ ID NO: 2:

( i ) SEQUENCE CHARACTERISTICS:
        ( A ) LENGTH: 8
        ( B ) TYPE: amino acid
        ( C ) STRANDEDNESS:
        ( D ) TOPOLOGY: linear ( x i ) SEQUENCE DESCRIPTION: SEQ ID NO: 2:

```
Asp  Thr  Arg  Pro  Ala  Pro  Gly  Ser
 1                  5
```

( 2 ) INFORMATION FOR SEQ ID NO: 3:

( i ) SEQUENCE CHARACTERISTICS:
        ( A ) LENGTH: 7
        ( B ) TYPE: amino acid
        ( C ) STRANDEDNESS:
        ( D ) TOPOLOGY: linear ( x i ) SEQUENCE DESCRIPTION: SEQ ID NO: 3:

```
Thr  Arg  Pro  Ala  Pro  Gly  Ser
 1                  5
```

(2) INFORMATION FOR SEQ ID NO: 4:

(i) SEQUENCE CHARACTERISTICS:
        (A) LENGTH: 7
        (B) TYPE: amino acid
        (C) STRANDEDNESS:
        (D) TOPOLOGY: linear (xi) SEQUENCE DESCRIPTION: SEQ ID NO: 4:

```
Asp  Arg  Pro  Ala  Pro  Gly  Ser
 1                  5
```

(2) INFORMATION FOR SEQ ID NO: 5:

(i) SEQUENCE CHARACTERISTICS:
        (A) LENGTH: 5
        (B) TYPE: amino acid
        (C) STRANDEDNESS:
        (D) TOPOLOGY: linear (xi) SEQUENCE DESCRIPTION: SEQ ID NO: 5:

```
Arg  Pro  Ala  Pro  Gly
 1                  5
```

(2) INFORMATION FOR SEQ ID NO: 6:

(i) SEQUENCE CHARACTERISTICS:
        (A) LENGTH: 10
        (B) TYPE: amino acid
        (C) STRANDEDNESS:
        (D) TOPOLOGY: linear (xi) SEQUENCE DESCRIPTION: SEQ ID NO: 6:

```
Val  Thr  Ser  Ala  Pro  Asp  Thr  Arg  Pro  Ala
 1                  5                        10
```

(2) INFORMATION FOR SEQ ID NO: 7:

(i) SEQUENCE CHARACTERISTICS:
        (A) LENGTH: 10
        (B) TYPE: amino acid
        (C) STRANDEDNESS:
        (D) TOPOLOGY: linear (xi) SEQUENCE DESCRIPTION: SEQ ID NO: 7:

```
Pro  Gly  Ser  Thr  Ala  Pro  Pro  Ala  His  Gly
 1                  5                        10
```

(2) INFORMATION FOR SEQ ID NO: 8:

(i) SEQUENCE CHARACTERISTICS:
        (A) LENGTH: 5
        (B) TYPE: amino acid
        (C) STRANDEDNESS:
        (D) TOPOLOGY: linear (xi) SEQUENCE DESCRIPTION: SEQ ID NO: 8:

```
Pro  Asp  Thr  Arg  Pro
 1                  5
```